United States Patent
Petrovich et al.

(10) Patent No.: US 6,972,553 B2
(45) Date of Patent: Dec. 6, 2005

(54) SENSOR READOUT CIRCUIT

(75) Inventors: Anthony Petrovich, Tewksbury, MA (US); John R. Williams, Lexington, MA (US); Christopher E. Dubé, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 10/075,754

(22) Filed: Feb. 14, 2002

(65) Prior Publication Data
US 2003/0151400 A1 Aug. 14, 2003

(51) Int. Cl.[7] ........................ G01R 23/00; G01R 29/22; G01G 3/16
(52) U.S. Cl. ................ 324/76.52; 324/727; 324/76.49; 73/580
(58) Field of Search .......................... 324/76.52–76.56, 324/727, 622, 617, 76.35, 76.49, 76.51, 71.1; 702/72, 75; 73/586, 24.06, 580

(56) References Cited

U.S. PATENT DOCUMENTS

| | | | |
|---|---|---|---|
| 3,828,607 A * | 8/1974 | Janzen et al. | 73/24.06 |
| 3,840,804 A * | 10/1974 | Sauerland | 324/727 |
| 4,447,782 A * | 5/1984 | Rutkoski | 324/727 |
| 5,283,037 A * | 2/1994 | Baer et al. | 422/82.01 |
| 5,444,641 A * | 8/1995 | White | 702/65 |
| 6,041,642 A * | 3/2000 | Duncan | 73/24.01 |
| 6,044,694 A * | 4/2000 | Anderson et al. | 73/54.41 |
| 6,106,149 A * | 8/2000 | Smith | 374/31 |
| 6,336,368 B1 * | 1/2002 | Chung et al. | 73/774 |
| 6,688,158 B2 | 2/2004 | Cunningham et al. | 73/24.06 |
| 6,820,469 B1 * | 11/2004 | Adkins et al. | 73/54.25 |
| 6,823,720 B1 * | 11/2004 | Adkins et al. | 73/54.25 |

OTHER PUBLICATIONS

Drever, R.W.P., et al., *Laser Phase and Frequency Stabilization Using an Optical Resonator*, Appl. Phys. B31, p. 97-105 (1983).

Pound, R.V., *Electronic Frequency Stabilization of Microwave Oscillators*, The Review of Scientific Instruments, vol. 17, No. 11, p. 490-505, Nov. 1946.

* cited by examiner

*Primary Examiner*—Anjan Deb
(74) *Attorney, Agent, or Firm*—Iandiorio & Teska

(57) ABSTRACT

A sensor readout circuit which provides a frequency signal output including a phase detector circuit responsive to an output signal from a sensor and an input signal to the sensor and configured to detect the phase difference between the input signal and the output signal, and a drive circuit responsive to the phase detector circuit and configured to maintain a fixed phase difference between the input signal and the output signal.

31 Claims, 8 Drawing Sheets

SENSOR READOUT CIRCUIT

FIELD OF THE INVENTION

This invention relates to a sensor readout circuit and more particularly to a sensor readout circuit which continuously outputs the resonance frequency of the sensor.

BACKGROUND OF THE INVENTION

The sensitivity of chemical and gravimetric sensors employing mass sensors, such as flexure plate wave resonators, is based on the sensitivity of the mass sensor velocity and resonant frequency to mass loading of the sensor. Many applications require that the resonant frequency of the sensor response be measured continuously to provide a measurement of any mass loading to the sensor. Readout of these sensors is complicated by the fact that multiple resonant peaks may be present in a typical response of the sensor.

In the prior art, one method for reading out the resonant frequency of a sensor is a swept frequency response measurement. The swept frequency response measurement technique relies on sweeping the frequency response of the sensor with a spectrum/network analyzer, measuring the magnitude voltage and phase angle of the response, and calculating if the chosen frequency represents the resonant frequency of the sensor.

However, this prior art technique has several disadvantages. Sweeping the frequency response of the sensor requires complex and expensive electronics which require substantial signal processing which can limit the rate of updating the sensor readout. Further, it is difficult to read out additional sensor characteristics, such as multiple resonant frequencies and resonant Q's associated with these resonances.

BRIEF SUMMARY OF THE INVENTION

It is therefore an object of this invention to provide an improved sensor readout circuit.

It is a further object of this invention to provide a sensor readout circuit which locks the input and output of the sensor at the same phase.

It is a further object of this invention to provide a sensor readout circuit which provides a continuous sensor output at the resonant frequency of a sensor.

It is a further object of this invention to provide a sensor readout circuit which eliminates the need to sweep the frequency response of a sensor to determine the resonant frequency of a sensor.

It is a further object of this invention to provide a sensor readout circuit which can isolate specific resonance frequencies when multiple resonant frequencies are present.

It is a further object of this invention to provide a sensor readout circuit which can easily determine the resonant Q of a sensor.

It is a further object of this invention to provide a sensor readout circuit which is inexpensive and compact in design.

This invention results from the realization that a truly effective sensor readout circuit can be achieved, not by sweeping the frequency response of a sensor, measuring the magnitude and phase shift at each chosen frequency, and then determining whether the chosen frequency represents the resonant frequency, but, instead by the combination of a unique phase detector circuit connected to an output and an input of the sensor which detects the phase difference between the input and an output signal of the sensor, and a drive circuit responsive to the phase detector circuit which maintains a fixed phase difference between the input signal and output signal to provide a continuous output of a frequency equal to the resonant frequency of the sensor.

This invention features a sensor readout circuit which provides a frequency signal output comprising a phase detector circuit connected to an output signal from a sensor and an input signal to the sensor and configured to detect the phase difference between the input signal and the output signal, and a drive circuit responsive to the phase detector circuit and configured to maintain a fixed phase difference between the input signal and the output signal. Ideally, the fixed phase difference between the input signal and the output signal is maintained at zero degrees. However, the fixed phase difference maintained by the drive circuit may be 90°, 180°, 270°, or any fixed phase difference between 0° and 360°. The sensor readout circuit may include a phase delay adjustment circuit responsive to the input signal and the phase detection circuit for adjusting the phase difference. Typically, the output signal is a sinusoidal voltage at a predetermined frequency. Typically the predetermined frequency is in the range of 10 MHz to 30 MHz.

In one embodiment, the sensor readout circuit includes a voltage step module configured to offset the input voltage by a predetermined amount to offset the frequency and measure the corresponding phase detector circuit output change. The input voltage maybe offset by 90°, 180°, 270°, or any voltage offset between 0° and 360°. The Q is calculated from the ratio of the offset of the voltage and the offset of the frequency.

In a preferred embodiment the sensor is a flexure plate wave device and continuously outputs a frequency representing the resonance frequency of the sensor.

This invention also features a method for determining the frequency signal output of a sensor, the method including the steps of: detecting the phase difference between an output signal from a sensor and an input signal to a sensor, and maintaining a fixed phase difference between the input signal and the output signal to a predetermined phase difference. In one example, the method for determining the frequency signal output of a sensor includes the step of adjusting the phase difference between the input signal and the output signal to a predetermined fixed phase difference.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

As discussed in the Background of the Invention above, one prior art technique for reading out the resonant frequency response of a sensitive mass sensor includes the use of a swept frequency response measurement. Using this technique, a frequency is chosen, the magnitude and phase angle of the response is measured, and a calculation is performed to determine if the resonant peak of the sensor is at the chosen frequency. The process is repeated until the frequency of the resonant peak of the sensor is found. The resonant frequency of the sensor, in turn, provides a measurement of any mass loading to the sensor.

Figure 1:
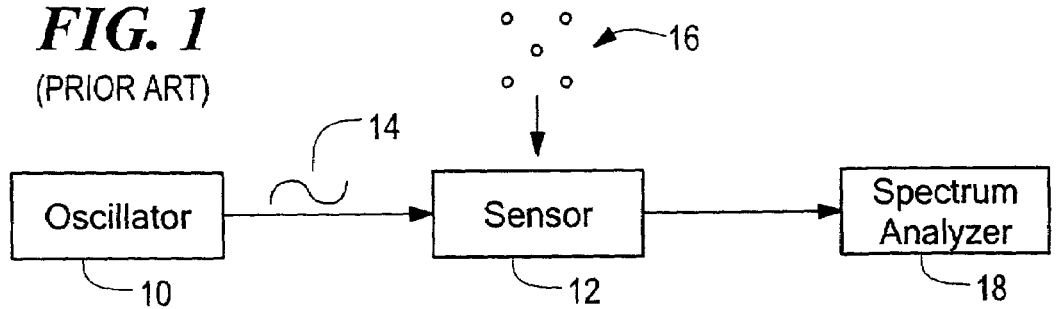
FIG. 1 is a block diagram showing one prior art method of reading out the resonant frequency of a sensor.

The prior art swept frequency response measurement technique employs oscillator 10, FIG. 1, to drive sensor 12, such as a flexure plate wave resonator, with sinusoidal voltage 14. Spectrum/network analyzer 18 measures the magnitude of voltage amplitude 22, FIG. 2, of the response of sensor 12 to sinusoidal voltage 14, FIG. 1 at a chosen frequency 20. Phase angle 24, FIG. 3 is then measured at frequency 20. To determine if frequency 20 represents the resonant peak of sensor 12, the phase discriminate, or zero voltage crossing, is calculated by the following equation:

$$\text{Phase discriminate} = V \cos(\phi) \quad (1)$$

where V is the magnitude of the response (e.g. magnitude of voltage amplitude 22, FIG. 2) and $\phi$ is the measured phase angle (e.g. phase angle 24, FIG. 3). If the response of sensor 12 is at the resonant peak it will be represented as discriminate zero voltage crossing, as shown by arrow 26, FIG. 4. However, in this example, at chosen frequency 20 the calculated phase discriminate is not at the zero voltage crossing, as shown by arrow 28. Therefore, frequency 20 does not represent the resonant frequency of sensor 12.

Accordingly, spectrum/network analyzer 18 continues to sweep the frequency, as shown by way of example at frequencies 30, 32, and 34, FIG. 1. At each chosen frequency, the magnitude and phase angle of sensor 12 is measured and a calculation using equation (1) is performed to determine if that frequency represents the resonant peak, i.e. the zero voltage crossing. Finally, and typically after substantial frequency sweeping, spectrum/network analyzer 18 measures magnitude of amplitude voltage 36, FIG. 1 at frequency 34 and phase angle 38, FIG. 2. The phase discriminate, or zero voltage crossing is calculated from magnitude of voltage amplitude 36 and phase angle 38 using equation (1) above. As shown in FIG. 3, frequency 34 represents the resonant frequency of the sensor because it is at zero voltage crossing 26.

Figure 2:
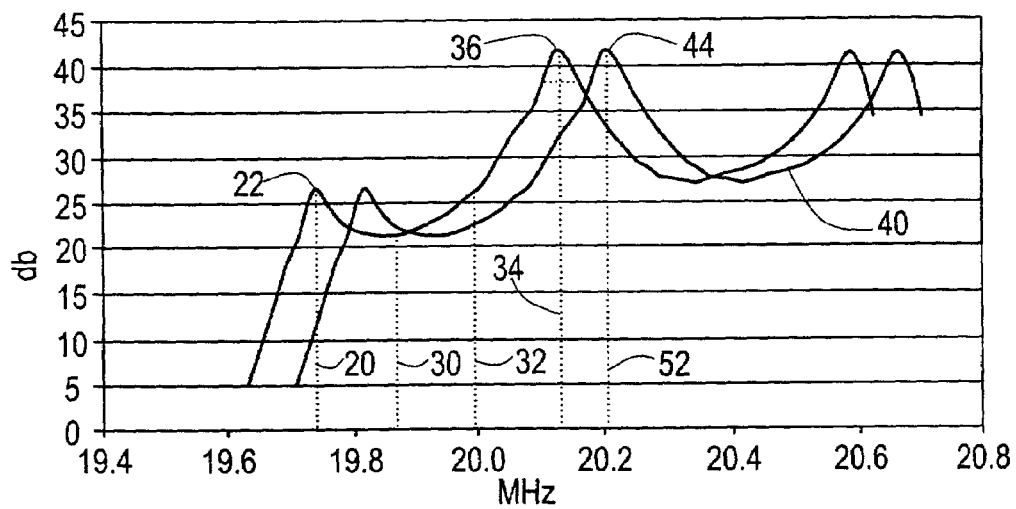
FIG. 2 is a graph showing the prior art measurement of the magnitude of a signal transmitted through the sensor of FIG. 1.
Figure 3:
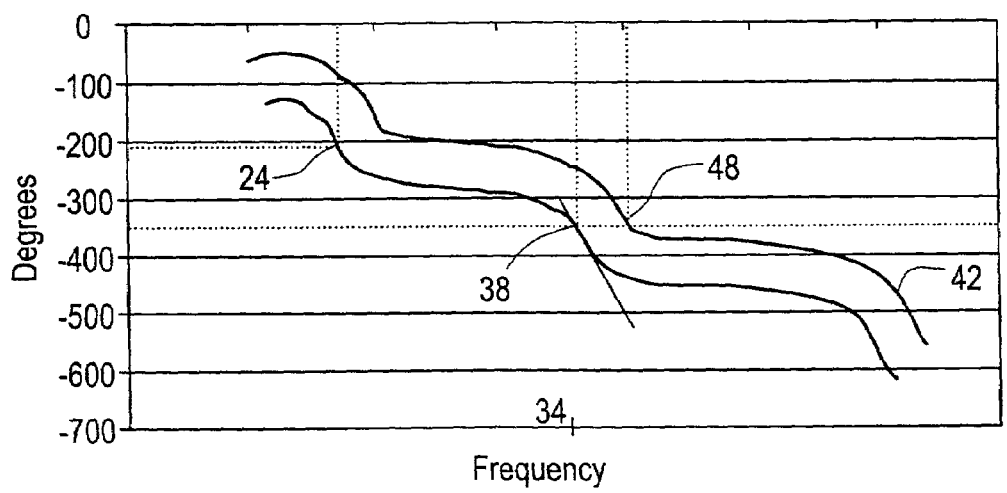
FIG. 3 is a graph showing the prior art measurement of the phase response of the signal transmitted through the sensor of FIG. 1.
Figure 4:
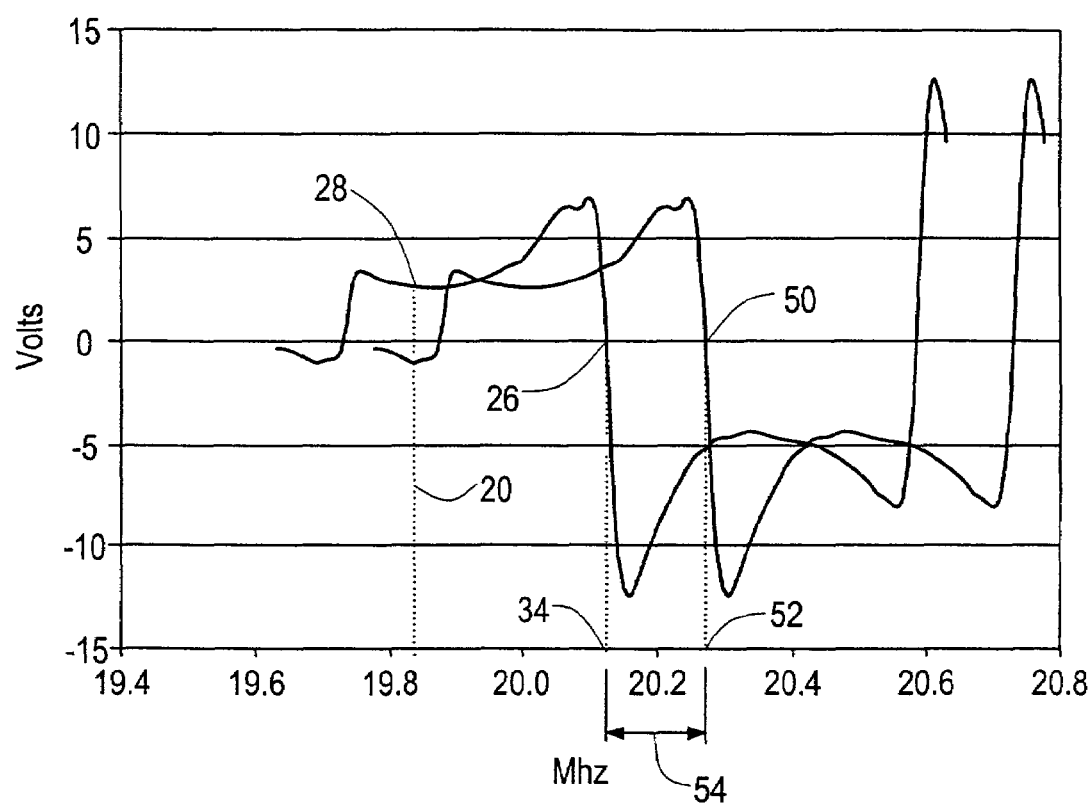
FIG. 4 is a graph showing the frequency of resonant peak of the sensor of FIG. 1 derived from the measured magnitude and phase response shown in FIGS. 2 and 3.

When sensor 12 is exposed to a mass loading, such as when analytes 16, FIG. 1 are loaded on sensor 12, the resulting mass change produces a voltage response as shown by graph 40, FIG. 2 and a phase response represented by graph 42, FIG. 3. The frequency is then swept until the frequency of the resonant peak is determined. For example, magnitude 44, FIG. 2, and phase angle 48, FIG. 3 are measured, and zero voltage crossing 50, FIG. 4 is calculated at resonant frequency 52. The change in mass resulting from mass loading sensor 12, FIG. 1 with analytes 16 is determined by difference in resonant frequency 52 after mass loading and resonant frequency 34 before mass loading, as shown by arrow 54.

Thus, the prior art technique of swept frequency response measurement to determine resonant frequency of sensor 12 requires sweeping the frequency with a spectrum/network analyzer, measuring the magnitude of the voltage and phase angle of the response for each chosen frequency, then determining by calculation if the chosen frequency represents the resonant frequency. This technique requires complex and expensive electronics, such as frequency spectrum/network analyzer 18, and requires substantial signal processing which can limit the rate of updating the sensor readout.

Figure 5:
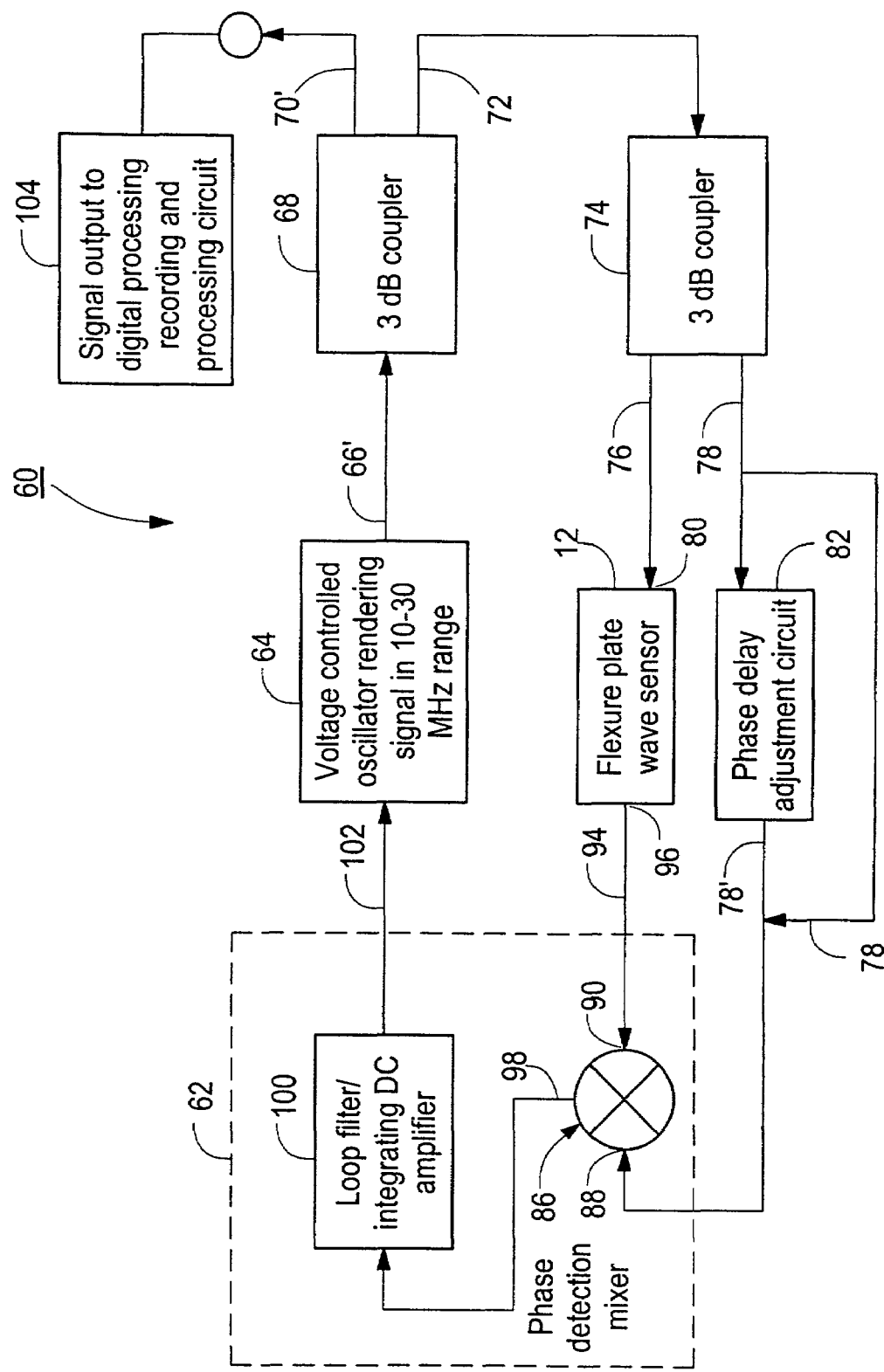
FIG. 5 is a block diagram of a sensor readout circuit according to the present subject invention.

In sharp contrast, novel sensor readout circuit 60, FIG. 5 of the subject invention locks drive circuit 64 to the phase shift at resonant frequency by unique phase detection circuit 62. By keeping the phase shift constant, the resonant frequency of the sensor will change as the mass on the sensor changes. Readout circuit 60 includes sensor 12 and phase detector circuit 62 interconnected with the input and output of sensor 12. Phase detector circuit 62 detects the phase difference between an input signal and an output signal to sensor 12. Drive circuit 64 is responsive to phase detector circuit 62 and maintains a fixed phase difference (e.g. zero degree phase delay) between the input signal and the output signal to sensor 12. Alternatively, the fixed phase difference between the input signal and output signal to sensor 12 may be 90°, 180°, 270°, or any fixed phase difference between 0° and 360°. Drive circuit 64, instead of sweeping the frequency as in the prior art, readout circuit 60 keeps the phase shift constant and measures the frequency change as the mass on the sensor changes. By locking or adjusting the phase delay to a predetermined phase, the phase at the resonant peak can be selected and the frequency corresponding to this peak can be continually tracked with the frequency of this operating point represented in the output signal. The output signal frequency is counted using standard digital frequency counting techniques and rendered in digital form to a digital processing and recording system. Moreover, with the addition of a voltage step module to offset the input voltage phase by a predetermined amount and measuring the resulting frequency offset, the resonant peak Q can be calculated from the ratio of the frequency and phase offsets.

Sensor readout circuit 60, FIG. 5 includes drive circuit 64, such as a voltage controlled oscillator, which generates signal on line 66 typically in the range of 10–30 MHz. The signal on line 66 is split by a 3 dB coupler 68 and one portion of the signal is provided as a first output signal on line 70 and the other portion is provided as second output signal on line 72. The signal on line 70 is rendered in digital form to a digital processing and recording system 104 and counted using standard digital frequency counting techniques known to those skilled in the art. The signal on line 72 is provided to second 3 dB coupler 74. Second 3 dB coupler 74 divides second output signal 72 into a signal on line 76 and phase reference signal on line 78. The signal on line 76 is input to sensor 12 at input 80 and the phase reference signal on line 78 is provided to optional phase delay adjustment circuit 82 which allows for phase shifting of the reference signal. Phase delay adjustment circuit may provide a voltage offset of 90°, 180°, 270°, or any voltage offset between 0° and 360°. The reference signal emerging directly from 3 dB coupler 74, or optionally, the reference signal on line 78' emerging from phase delay adjustment circuit 82, is provided to phase detector circuit 62 which is responsive to drive circuit 64 and maintains a fixed phase difference between the input signal on line 76 to sensor 12 and the output signal on line 94 from sensor 12. The fixed phase difference may be 0°, 90°, 180°, 270°, or any fixed phase difference between 0° and 360°. Phase detector circuit 62 typically includes phase detection mixer 86 and loop filter/integrating DC amplifier 100. The output signal on line 78 is provided to L signal port 88 of phase detection mixer 86.

In one preferred example, the output signal on line 78' from phase delay adjustment circuit 82 is provided to L signal port 88 of phase detection mixer 86. The output signal on line 94 from sensor 12 is provided to R signal port 90. The signal on line 98 from phase detector mixer 86 is provided to loop filter/integrating DC amplifier 100 which provides a baseband feedback signal on line 102 to drive circuit 64 to lock drive circuit 64 at the output signal on line 66 which has fixed phase difference (e.g., zero phase delay) between the input signal on line 76 and output signal on line 94 of sensor 12.

Thus, instead of sweeping the frequency, measuring the magnitude and phase angle at each frequency, and then performing calculations to determine the resonant frequency as swept in the prior art, the sensor readout circuit of the subject invention employs unique phase detection circuit 62 to lock drive circuit 64 to the phase shift of sensor 12 at the resonant frequency. By keeping the phase shift constant, the resonant frequency of the sensor will thus change as the mass on sensor 12 changes. The result is a more robust sensor readout circuit which better measures the resonant frequency response to mass loading on sensor 12. At the same time, the sensor readout circuit of this invention is simple in design, inexpensive, and does not require substantial signal processing which can limit the rate of updating the sensor readout.

Figure 6A:
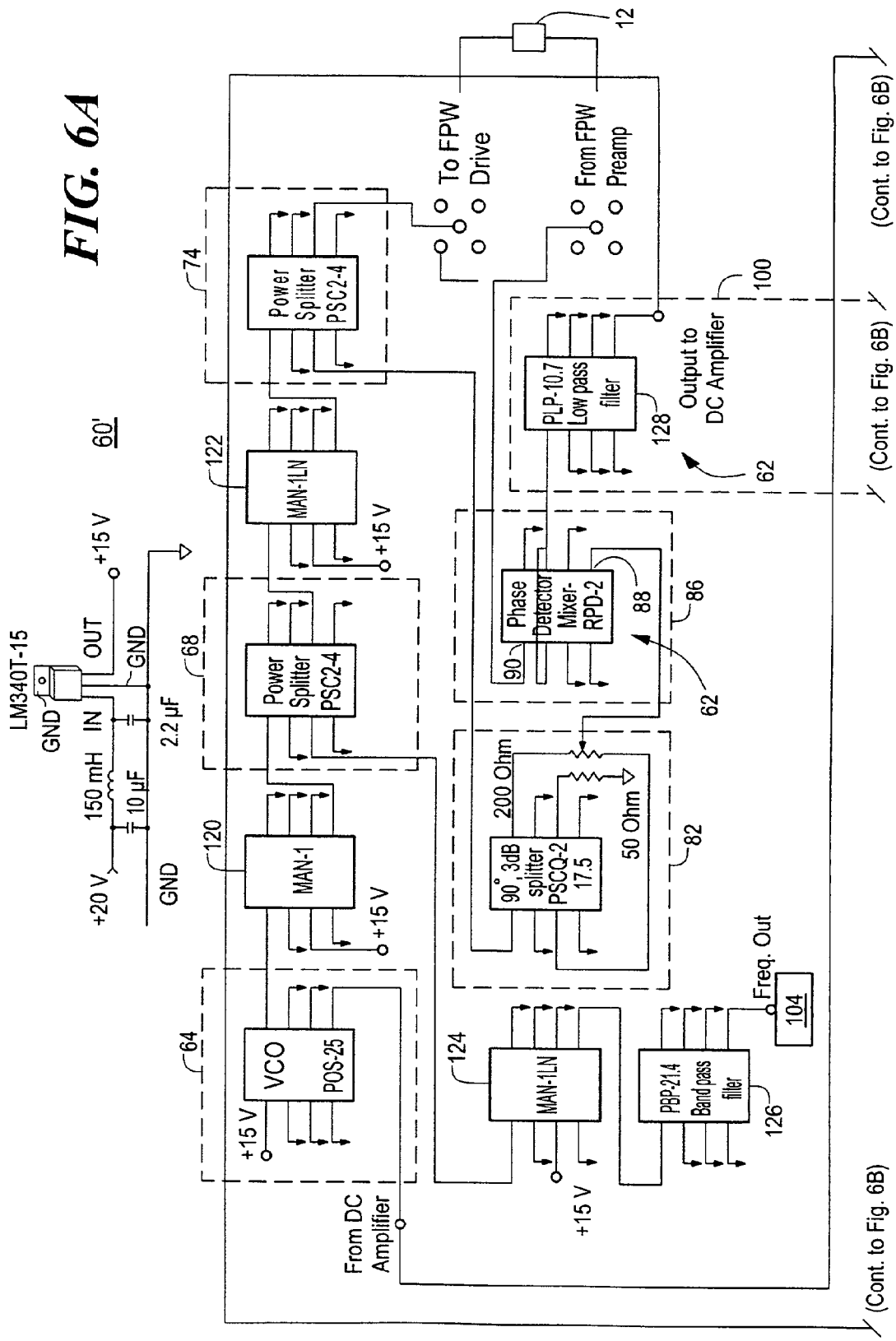
FIG. 6 is a more detailed schematic diagram of one embodiment of the sensor readout circuit of FIG. 5.
Figure 6B:
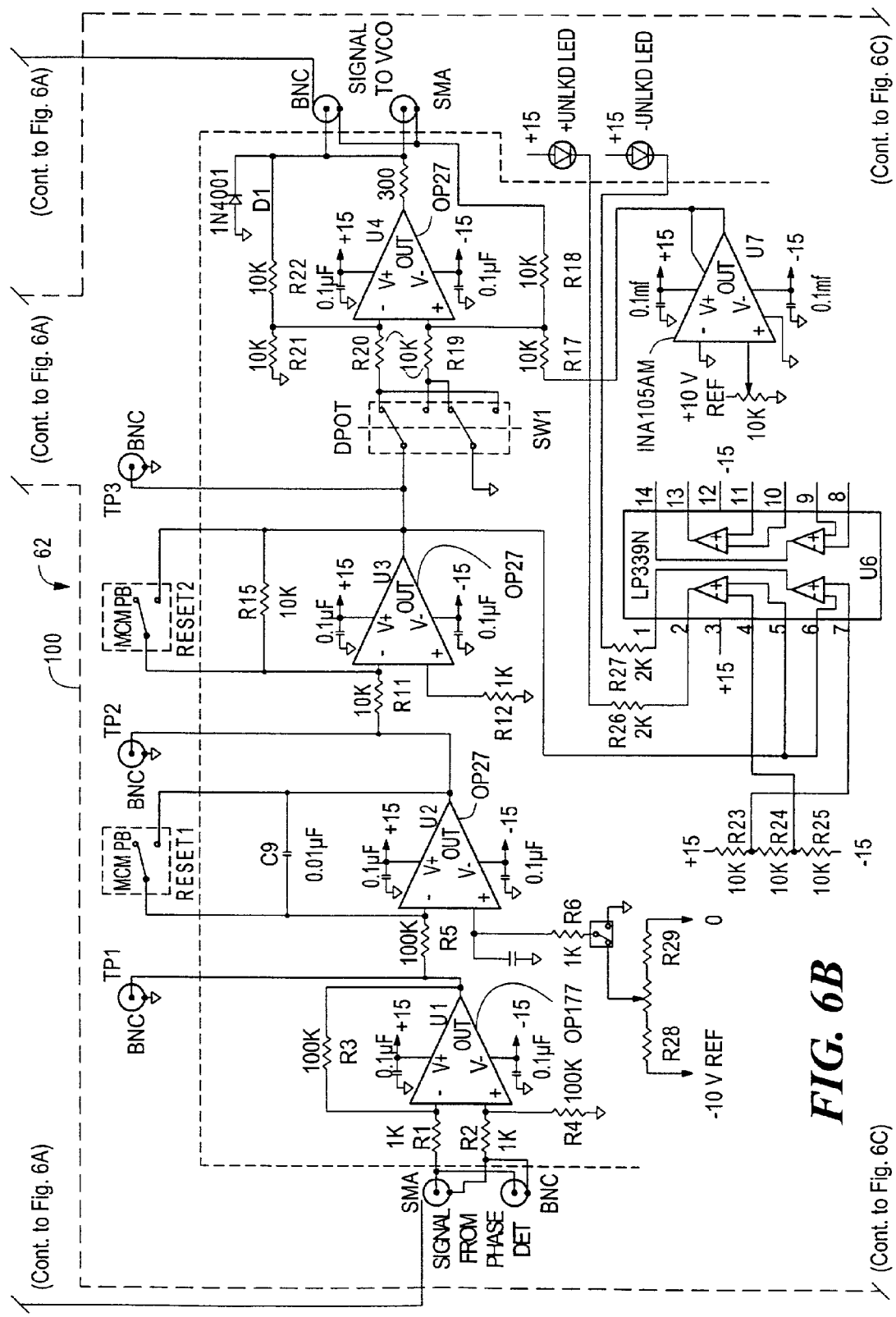
Figure 6C:
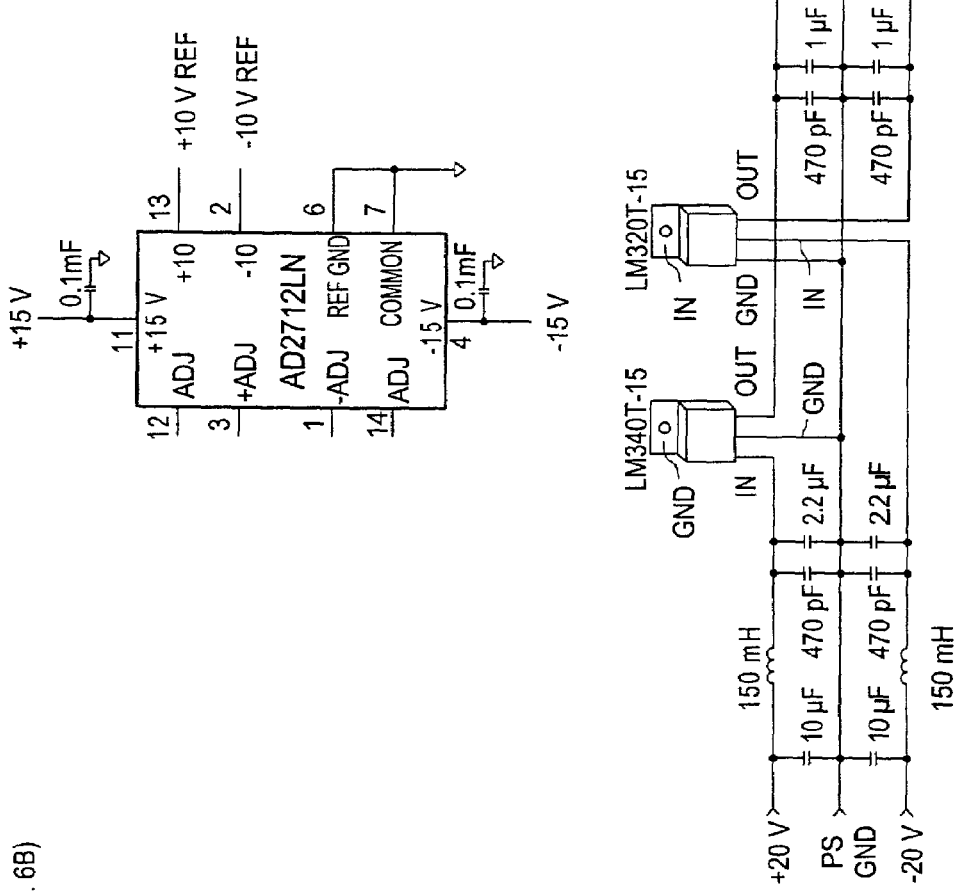

There is shown in FIG. 6 a more detailed schematic diagram of one example of the sensor readout circuit shown in FIG. 5 useful in connection with a flexure plate wave resonator. Sensor readout circuit 60' similarly locks drive circuit 62 to the phase shift at resonant frequency and, by keeping the phase shift constant, the frequency of the sensor will change as the mass on the sensor changes.

Sensor readout circuit 60', FIG. 6 includes voltage controlled oscillator 64 which generates a phase locked signal which is amplified by amplifier 120. Amplifier 120 provides a signal to first 3 dB coupler 68 which splits the signal between amplifier 122 and amplifier 124. Amplifier 122 amplifies the signal from first 3 dB coupler 68 and provides an amplified signal to second 3 dB coupler 74. Amplifier 124 receives a signal from first 3 dB coupler 68 and provides an amplified signal to band pass filter 126. Band pass filter 126 provides a signal in digital form to a digital processing and recording system 104 which is counted using standard digital frequency counting techniques. Second 3 db coupler 74 splits the signal received from amplifier 122 between sensor 12 and phase delay adjustment circuit 82. Phase detection circuit 62 receives an input signal from phase delay adjustment circuit 82 and includes phase detection mixer 86, low pass filter 128 and loop filter 100. Phase detection mixer 86 receives an input signal from phase delay adjustment circuit 82 at L signal port 88 and a second input signal at R signal port 90 from sensor 12. The output signal emerging from phase detection mixer 86 is provided to low pass filter 128 which provides an input signal to loop filter 100. Phase detection circuit 62 provides a baseband feedback signal to voltage controlled oscillator 64 to lock voltage controlled oscillator at an output signal which has fixed phase difference (e.g., zero phase delay) between the input signal and output signal of sensor 12.

Figure 7:
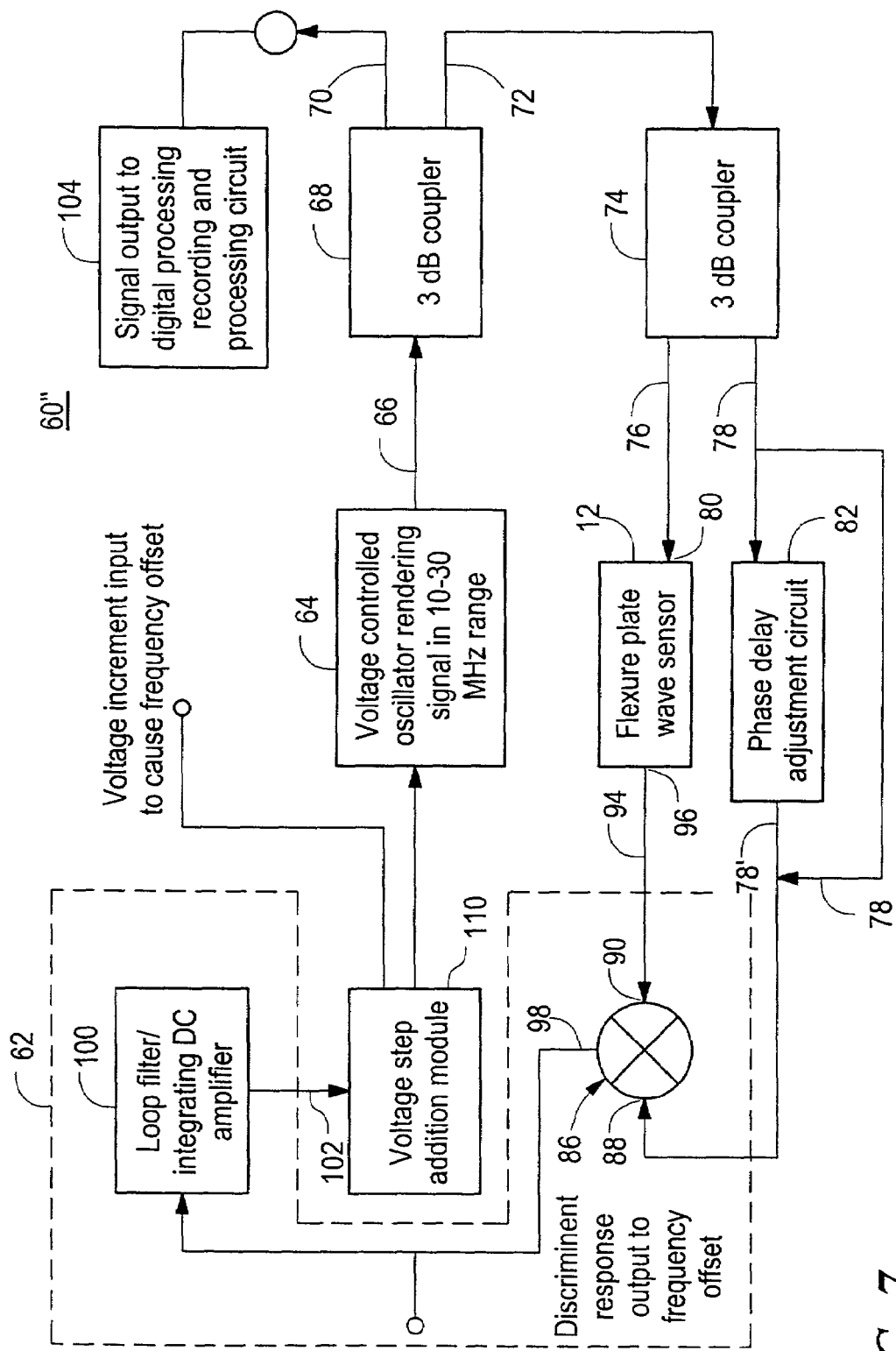
FIG. 7 is a block diagram of another embodiment of the sensor readout circuit according to the present invention similar to the system shown in FIG. 5, showing additional circuitry to measure resonant peak Q.
Figure 8:
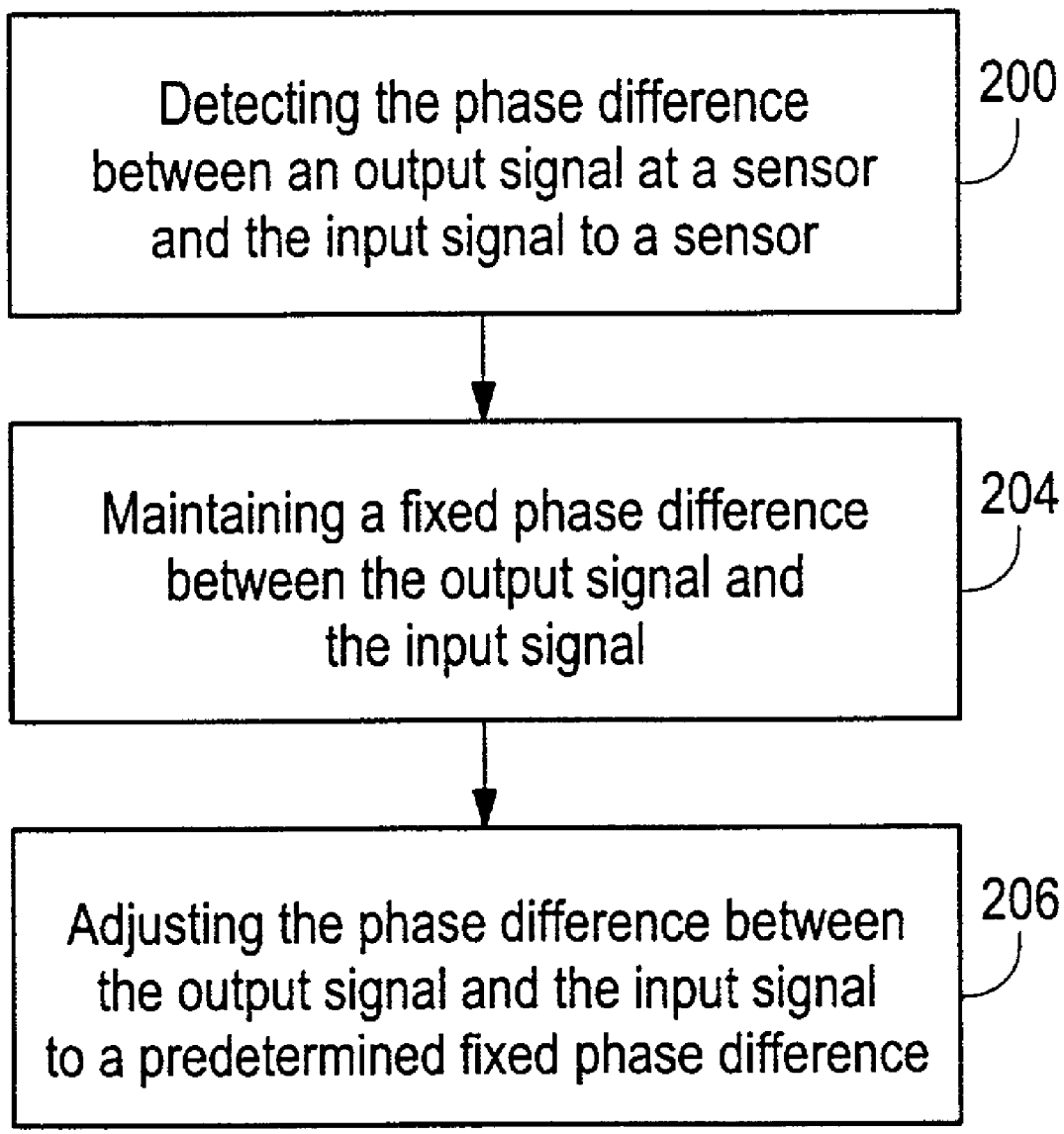
FIG. 8. is a flow chart of one embodiment of the method to read out a sensor in accordance with the present invention.

In another embodiment in accordance with the subject invention, readout circuit 60", FIG. 7 includes all of the circuitry of sensor readout circuit 60, FIG. 5, but also includes voltage step module 110 to provide for measurement of resonant peak Q as well as the resonant frequency. Resonant peak Q measurement is accomplished by first locking the drive circuit 64 to the resonant frequency of sensor 12 as described above. Baseband feedback signal 102 is interrupted and a voltage step is applied to voltage controlled oscillator 64 by voltage step module 110 to offset the operating condition of sensor 12 by a specific phase increment, such as 90°, 180° or 270°. However, any phase increment may be chosen between 0 and 360°. The resulting frequency offset is measured and the Q is calculated from the ratio of frequency and phase offsets.

The unique design of sensor readout circuit 60" with voltage step addition module 110 provides a continuous frequency readout throughout the phase locking of drive circuit 64 to the transmission resonant operating point of sensor 12. Sensor readout circuit 60" can be adjusted by biasing drive circuit 64 to lock to alternate resonant peaks and provide measurement of resonant Q by offsetting the feedback loop phase delay and measuring the output frequency offset.

The preferred method for determining the frequency signal output of a sensor includes the steps of: detecting the phase difference between an output signal from a sensor and an input signal to a sensor, step 200, FIG. 7 and maintaining a fixed phase difference between the output signal and the input signal, step 202. In one example, the method also includes adjusting the phase difference between the input signal and the output signal, step 204.

The unique combination of a phase detection circuit and a drive circuit (e.g. a voltage controlled oscillator) results in a robust readout circuit which fixes the drive circuit to maintain a specific phase delay between the output and the input of the sensor. By locking or adjusting the phase delay, the phase at the resonant peak can be selected and the frequency corresponding to this peak can be continually tracked with the frequency represented as an output signal which is counted using standard digital frequency counting techniques and rendered in digital form to a digital processing and recording system. There is no need to sweep the frequency, measure the magnitude and phase angle and perform calculations as found in the prior art. Instead, a predetermined phase shift is maintained, and the corresponding change in the resonant frequency is easily measured. In this invention, there is no need for expensive and complex electronics, such as a spectrum/network analyzer, which requires substantial signal processing and limits the rate of updating the sensor readout circuit. The sensor readout circuit of the subject invention is robust and inexpensive and compact in design, provides frequent updates to the sensor response, and can be used in compact flexure plate wave chemical and gravimetric sensor units.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims.

What is claimed is:

1. A sensor readout circuit which provides a frequency signal output, the readout circuit comprising:
a phase detector circuit responsive to an output signal from a sensor and an input signal to the sensor and configured to detect the phase difference between the input signal and the output signal; and
a drive circuit responsive to the phase detector circuit and configured to maintain a fixed phase difference between the input signal and the output signal.

2. The sensor readout circuit of claim 1 in which the fixed phase difference between the input signal and the output signal is maintained at zero degrees by the drive circuit.

3. The sensor readout circuit of claim 1 in which the fixed phase difference between the input signal and the output signal is maintained at 90° by the drive circuit.

4. The sensor readout circuit of claim 1 in which the fixed phase difference between the input signal and the output signal is maintained at 180° by the drive circuit.

5. The sensor readout circuit of claim 1 in which the fixed phase difference between the input signal and the output signal is maintained at 270° by the drive circuit.

6. The sensor readout circuit of claim 1 in which the fixed phase difference between the input signal and the output signal is maintained at a fixed phase difference between 0° and 360° by the drive circuit.

7. The sensor readout circuit of claim 1 further including a phase delay adjustment circuit responsive to the input signal and the phase detection circuit for adjusting the phase difference between the input signal and the output signal.

8. The sensor readout circuit of claim 1 in which the output signal is a sinusoidal voltage at a predetermined frequency.

9. The sensor readout circuit of claim 8 in which the predetermined frequency is in the range of 10 MHz to 30 MHz.

10. The circuit of claim 9 in which the Q is calculated from the ratio of the offset of the voltage and the offset of the frequency.

11. The sensor readout circuit of claim 8 further including a voltage step module configured to offset the input voltage by a predetermined amount to offset the frequency and measure the corresponding phase detector circuit output change.

12. The sensor readout circuit of claim 11 in which input voltage is offset 90°.

13. The sensor readout circuit of claim 11 in which input voltage is offset 180°.

14. The sensor readout circuit of claim 10 in which input voltage is offset 270°.

15. The sensor readout circuit of claim 1 in which the sensor readout circuit continuously outputs a frequency representing the resonance frequency of the sensor.

16. A sensor readout circuit which provides a frequency signal output, the readout circuit comprising:
a phase detector circuit responsive to an output signal from a sensor and an input signal to the sensor and configured to detect the phase difference between the input signal and the output signal;
a drive circuit responsive to the phase detector circuit and configured to maintain a fixed phase difference between the input signal and the output signal; and
a phase delay adjustment circuit responsive to the input signal and the phase detection circuit for adjusting the phase difference.

17. A sensor readout circuit which provides a frequency signal output, the readout circuit comprising:
a phase detector circuit responsive to an output signal from a sensor and an input signal to the sensor and configured to detect the phase difference between the input signal and the output signal; and
a drive circuit responsive to the phase detector circuit and configured to maintain a fixed phase difference between the input signal and the output signal; and
a voltage step module configured to offset the voltage by a predetermined amount to offset the frequency and measure the corresponding phase detector circuit output change.

18. The circuit of claim 17 in which the Q is calculated from the ratio of the offset of the voltage and the offset of the frequency.

19. A sensor readout circuit which provides a frequency signal output, the readout circuit comprising:
a phase detector circuit responsive to an output signal from a sensor and an input signal to the sensor and configured to detect the phase difference between the input signal and the output signal;
a drive circuit responsive to the phase detector circuit and configured to maintain a fixed phase difference between the input signal and the output signal;
a phase delay adjustment circuit responsive to the input signal and the phase detection circuit for adjusting the phase difference; and
a voltage step module configured to offset the voltage by a predetermined amount to offset the frequency and measure the corresponding phase detector circuit output change.

20. A sensor readout circuit which provides a frequency signal output, the readout circuit comprising:
a phase detector circuit responsive to an output signal from a flexure plate wave device and an input signal to the flexure plate wave device and configured to detect the phase difference between the input signal and the output signal; and
a drive circuit responsive to the phase detector circuit and configured to maintain a fixed phase difference between the input signal and the output signal.

21. The sensor readout circuit of claim 20 in which the fixed phase difference between the input signal and the output signal is maintained at zero degrees by the drive circuit.

22. The sensor readout circuit of claim 20 in which the fixed phase difference between the input signal and the output signal is maintained at 90° by the drive circuit.

23. The sensor readout circuit of claim 20 in which the fixed phase difference between the input signal and the output signal is maintained at 180° by the drive circuit.

24. The circuit of claim 23 further including a voltage step module configured to offset the voltage by a predetermined amount to offset the frequency and measure the corresponding phase detector circuit output change.

25. The sensor readout circuit of claim 20 in which the fixed phase difference between the input signal and the output signal is maintained at 270° by the drive circuit.

26. The sensor readout circuit of claim 20 in which the fixed phase difference between the input signal and the output signal is maintained at a fixed phase difference between 0° and 360° by the drive circuit.

27. The sensor readout circuit of claim 20 further including a phase delay adjustment circuit responsive to the input signal and the phase detection circuit for adjusting the phase difference.

28. The sensor readout circuit of claim 20 in which the output signal is a sinusoidal voltage at a predetermined frequency.

29. The sensor readout circuit of claim 20 in which the sensor readout circuit continuously outputs a frequency representing the resonance frequency of the flexure plate wave device.

30. A method for determining the frequency signal output of a sensor, the method comprising the steps of:
   detecting the phase difference between an output signal from a sensor and an input signal to a sensor; and
   maintaining a fixed phase difference between the input signal and the output signal.

31. A method for determining the frequency signal output of a sensor, the method comprising:
   detecting the phase difference between an output signal from a sensor and an input signal to a sensor;
   maintaining a fixed phase difference between the input signal and the output signal; and
   adjusting the phase difference between the input signal and the output signal to a predetermined fixed phase difference.

* * * * *